United States Patent [19]

Schröder et al.

[11] Patent Number: 4,457,870

[45] Date of Patent: Jul. 3, 1984

[54] REGULATING PLANT GROWTH WITH NOVEL 1-AMINO-CYCLOPROPANECARBOXYLIC ACID METAL COMPLEXES

[75] Inventors: Rolf Schröder, Wuppertal-Elberfield; Klaus Lürssen, Bergisch–Gladbach, both of Fed. Rep. of Germany

[73] Assignee: Bayer Aktiengesellschaft, Leverkusen, Fed. Rep. of Germany

[21] Appl. No.: 406,680

[22] Filed: Aug. 9, 1982

[30] Foreign Application Priority Data

Aug. 27, 1981 [DE] Fed. Rep. of Germany ....... 3133917

[51] Int. Cl.³ .......................... C07F 11/00; C07F 3/06; C07F 15/02; C07F 15/04
[52] U.S. Cl. .............................. 260/429 R; 260/429.9; 260/438.1; 260/439 R; 71/97
[58] Field of Search ............. 260/429.9, 429 R, 438.1, 260/429 J

[56] References Cited

U.S. PATENT DOCUMENTS

| | | | |
|---|---|---|---|
| 3,644,448 | 2/1972 | O'Neill | 260/429 J X |
| 3,687,992 | 8/1972 | Feiler et al. | 260/429 J X |
| 3,719,694 | 3/1973 | Feiler et al. | 260/429 J X |
| 3,958,972 | 5/1976 | Magin | 260/429 J X |
| 4,152,345 | 5/1979 | Gaudette et al. | 260/429 J X |
| 4,216,143 | 8/1980 | Ashmead | 260/429 J X |

FOREIGN PATENT DOCUMENTS 0005782 12/1979 European Pat. Off. .
0030287 6/1981 European Pat. Off. .

OTHER PUBLICATIONS

Chemical Abstracts 96(6), 45284u, (1981).

*Primary Examiner*—Helen M. S. Sneed
*Attorney, Agent, or Firm*—Sprung, Horn, Kramer & Woods

[57] ABSTRACT

1-Amino-cyclopropanecarboxylic acid metal complexes of the formula

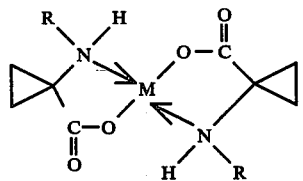

in which
R is a hydrogen atom or a radical of the formula $-CO-R^1$,
$R^1$ is a hydrogen atom or an alkyl or phenyl radical, and
M is a transition metal atom which can assume the coordination number 4 which possess plant growth regulating activity.

11 Claims, No Drawings

REGULATING PLANT GROWTH WITH NOVEL 1-AMINO-CYCLOPROPANECARBOXYLIC ACID METAL COMPLEXES

The invention relates to certain new 1-amino-cyclopropanecarboxylic acid metal complex compounds, to a process for their production and to their use as plant growth regulators.

It has already been disclosed that certain 1-amino-cyclopropane-1-carboxylic acid derivatives are suitable for regulating plant growth (see German Published Specification DOS 2,824,517). Thus, for example, 1-amino-cyclopropane-1-carboxylic acid hydrochloride can be used for influencing plant growth. However, the action of this substance is not always satisfactory in every respect, in particular when low amounts are used.

The present invention now provides, as new compounds, the 1-amino-cyclopropanecarboxylic acid metal complex compounds of the general formula

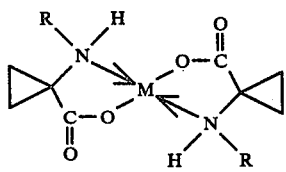

(I)

in which

R represents a hydrogen atom or a radical of the general formula —CO—$R^1$, wherein $R^1$ represents a hydrogen atom or an alkyl or phenyl radical and M represents a transition metal atom which can assume the coordination number 4.

According to the present invention we further provide a process for the production of a compound of the present invention characterized in that a cyclopropanecarboxylic acid derivative of the general formula

(II)

in which

R has the meaning given above, is reacted with a transition metal compound of the general formula

MZ     (III)

in which

M has the meaining given above and

Z represents oxygen, carbonate, sulphate, two hydroxyl groups or two halide ions, in the presence of a diluent.

The compounds of the present invention are distinguished by powerful plant growth-regulating properties.

Surprisingly, the compounds according to the present invention possess a better plant growth-regulating activity than 1-amino-cyclopropane-1-carboxylic acid hydrochloride, which is a constitutionally similar previously known active compound with the same direction of action.

Preferred compounds according to the present invention are those in which

R represents a hydrogen atom or a radical of the general formula —CO—$R^1$, wherein $R^1$ represents a hydrogen atom, an alkyl radical having 1 to 4 carbon atoms or a phenyl radical, and M preferably represents copper, zinc, manganese, iron, cobalt or nickel.

A particularly peferred group of compounds according to the present invention are those in which R represents a hydrogen atom or a formyl radical, and M represents copper, zinc, or manganese.

A further group of particularly preferred compounds according to the present invention are those in which R represents a hydrogen atom or a formyl radical, and M represents iron, cobalt or nickel.

Finally, those compounds according to the present invention are also particularly preferred, in which R represents a radical of the general formula —CO—$R^1$, wherein $R^1$ represents a methyl, ethyl, n-propyl, iso-propyl, n-butyl, iso-butyl, sec.-butyl, tert.-butyl, or phenyl radical, and M represents copper, zinc, manganese, iron cobalt or nickel.

If, for example, 1-formylamino-cyclopropane-1-carboxylic acid and manganese (II) sulphate are used as starting materials, the course of the process according to the invention can be represented by the following equation.

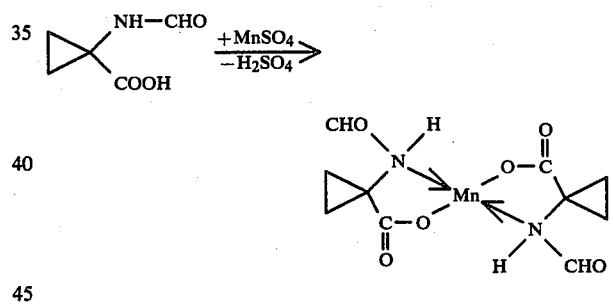

Preferred cyclopropanecarboxylic acid derivatives of formula (II) required as starting materials in the process according to the invention are those in which R has those meanings which have already been mentioned for this radical in connection with the description of the preferred and particularly preferred substances according to the present invention.

The following may be mentioned as examples of compounds of the formula (II):

1-amino-cyclopropane-carboxylic acid,
1-formylamino-cyclopropanecarboxylic acid,
1-acetylamino-cyclopropanecarboxylic acid and
1-benzoylamino-cyclopropanecarboxylic acid.

The compounds of the formula (II) are already known (see German Published Specification DOS No. 2,824,517).

Preferred transition metal compounds of formula (III) further required as starting materials in the process according to the invention are those in which M has that meaning which has already been mentioned for this radical in connection with the description of the preferred and particularly preferred compounds according to the present invention, and Z represents oxygen, carbonate, sulphate, two hydroxyl groups, two chloride ions or two bromide ions.

The following may be mentioned as examples of the starting compounds of the formula (III):

manganese (II) oxide, manganese (II) carbonate, zinc (II) oxide, zinc (II) carbonate and copper (II) oxide.

The compounds of the formula (III) are known.

The process according to the invention is carried out in the presence of a diluent. Protic polar solvents are preferred diluents. These include, in particular, water and alcohols (such as methanol, ethanol and propanol). Water is a particularly preferred solvent.

In the process according to the invention, the reaction temperature can be varied within a relatively wide range. The reaction is carried out in general at a temperature between 0° and 100° C., preferably between 20° and 100° C. The process according to the invention is carried out in general under normal pressure.

To carry out the process according to the invention in general between 0.5 and 1 mol, preferably between 0.55 and 0.8 mol, of the starting compound of the formula (III) is employed per mol of starting compound of the formula (II). The starting materials are generally mixed with the diluent, and stirred until the end of the reaction, if appropriate at an elevated temperature. Working-up is effected according to customary methods. In general, the procedure is as follows: the reaction mixture which is still hot is filtered, the filtrate is cooled, and the product is precipitated, if appropriate by the addition of an organic diluent, such as, for example, acetone, and is isolated by filtering off under suction.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds, at merges, at airports or in fruit orchards. The inhibition of growth of herbaceous and woody plants at merges, and in the vicinity of pipelines or overland lines, or quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging. The use of growth regulators for shortening and strengthening the stems enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefits blossoming and fruit formation to a greater extent that they benefit the vegative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by effecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time as achieved. Such defoliation is of great importance in the mechanical harvesting of cotton, but it is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes, or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions foams, suspensions, wettable powders, pastes, soluble powders, dusting agents and granules. They may be used in the customary manner, for example by watering, spraying, atomizing, scattering, dusting, foaming and coating. Furthermore, it is possible to apply the active compounds in accordance with the ultra-low volume process or to inject the active compound preparation or the active compound itself into the soil. It is also possible to treat the seeds of the plants.

The amounts applied can be varied within a substantial range. In general, 0.01 to 50 kg, preferably 0.05 to 10 kg of the active compound are employed per hectare of soil surface.

The present invention also provides plant-growth regulating composition containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the substances according to the invention is evident from the example which follow.

PREPARATIVE EXAMPLES

EXAMPLE 1

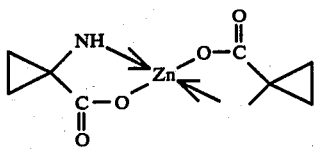
(1)

4.4 g (35 mmol) of zinc carbonate were added to a solution of 5.0 g (50 mmol) of 1-amino-cyclopropanecarboxylic acid in 50 ml of water, and the mixture was heated at the boil under reflux for 4 hours. The mixture was then filtered while hot, the filtrate was cooled, and the product was precipitated with acetone and isolated by filtration. 5.6 g (85% of theory) of the zinc complex of 1-amino-cyclopropanecarboxylic acid represented by the above formula were obtained in the form of a white powder.

The compounds of the formula (I) which were listed as formulae in Table 1 below were also prepared in the manner given in Example 1. In the synthesis of the manganese complex compounds, in which manganese(II) carbonate was employed in each case as the starting material of the formula (III), the reaction was carried out under a nitrogen atmosphere in each case. The melting points of the products could not be determined exactly, owing to the onset of decomposition or sublimation of the products.

TABLE 1

| | | | (I) |
|---|---|---|---|

| Compound No. | R | M | Yield (% of theory) |
|---|---|---|---|
| 2 | H | Mn | 86 |
| 3 | H | Cu | 86 |
| 4 | CHO | Mn | 95 |
| 5 | CHO | Zn | 89 |

The plant-growth regulant activity of the compounds of this invention is illustrated by the following biotest examples.

In these examples the compounds according to the present invention are each identified by the number (given in brackets) from Example 1 and Table 1.

The known comparison compound is identified as follows:

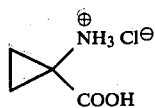

1-Amino-cyclopropane-1-carboxylic acid hydrochloride (disclosed in German Published Specification DOS 2,824,517)

EXAMPLE 2

Formation of ethylene

Solvent: 30 parts by weight of dimethylformamide
Emulsifier: 1 part by weight of polyoxyethylene sorbitane monolaurate To produce a suitable preparation of active compound, 1 part by weight of active compound was mixed with the stated amounts of solvent and emulsifier and the mixture was made up to the desired concentration with water.

Pieces of leaf of identical size were punched from soybean leaves. These were introduced into vials which could be closed air-tight, together with 1 ml of the preparation of active compound or control solution. After 24 hours the ethylene which had collected in the vials was determined by customary methods of detection. The evolution of ethylene from the pieces of leaf treated with the preparations of active compound was compared with the evolution of ethylene from the controls.

The figures of merit had the following meanings:
0 denoted evolution of ethylene as in the case of the control
+ denoted the slightly increased evolution of ethylene
++ denoted greatly increased evolution of ethylene
+++ denoted very greatly increased evolution of ethylene In this test, the compounds (1), (2), (3) and (5) showed a very powerful action, and the compound (4) shows a powerful action.

EXAMPLE 3

Stimulation of the fixation of $CO_2$ in soybeans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Soybeans were grown in a greenhouse until the first secondary leaf had completely unfolded. At this stage, the plants were sprayed with the preparations of active compound until dripping wet. In the further course of the experiment, the fixation of $CO_2$ in the plants was determined by customary methods. The values were compared with those of the control plants, which had not been treated with the active compounds.

The figures of merit had the following meanings:
− denoted inhibition of the fixation of $CO_2$
0 denoted fixation of $CO_2$ as in the case of the control
+ denoted low stimulation of the fixation of $CO_2$
++ denoted powerful stimulation of the fixation of $CO_2$
+++ denoted very powerful stimulation of the fixation of $CO_2$ In this test, the compound (3) caused a substantially more powerful stimulation of the fixation of $CO_2$ than the comparative substance (A).

It will be understood that the specification and examples are illustrative but not limitative of the present invention and that other embodiments within the spirit and scope of the invention will suggest themselves to those skilled in the art.

What is claimed is:

1. A 1-amino-cyclopropanecarboxylic acid metal complex of the formula

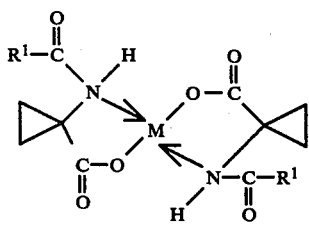

in which
R¹ is a hydrogen atom or an alkyl or phenyl radical, and
M is a transition metal atom which can assume the coordination number 4.

2. A complex according to claim 1, in which
R¹ is a hydrogen atom or an alkyl radical having 1 to 4 carbon atoms or a phenyl radical, and
M is copper, zinc, manganese, iron, cobalt or nickel.

3. A complex according to claim 1, in which
R¹ is a formyl radical, and
M is copper, zinc, or manganese.

4. A complex according to claim 1, in which
R¹ is a formyl radical, and
M is iron, cobalt or nickel.

5. A complex according to claim 1, wherein such complex is the manganese complex of 1-formylamino-cyclopropanecarboxylic acid of the formula

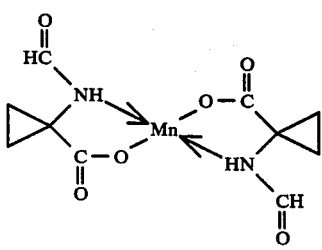

6. A complex according to claim 1, wherein such complex is the zinc complex of 1-formylamino-cyclopanecarboxylic acid of the formula

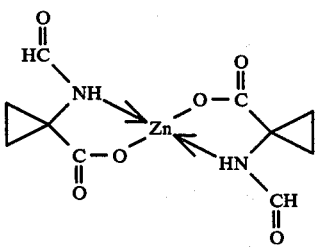

7. A 1-amino-cyclopropanecarboxylic acid metal complex of the formula

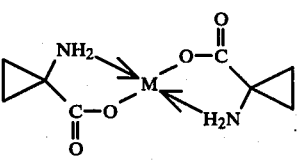

in which
M is zinc, manganese, iron, cobalt or nickel.

8. A complex according to claim 7, in which M is zinc or manganese.

9. A complex according to claim 7, in which M is iron, cobalt or nickel.

10. A complex according to claim 7, wherein such complex is the zinc complex of 1-amino-cyclopropanecarboxylic acid of the formula

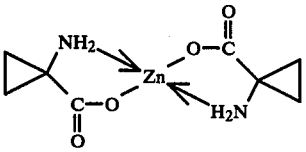

11. A complex according to claim 7, wherein such complex is the manganese complex of 1-amino-cyclopropanecarboxylic acid of the formula

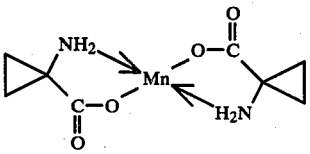

* * * * *